(12) United States Patent
Malowaniec

(10) Patent No.: US 6,428,525 B1
(45) Date of Patent: Aug. 6, 2002

(54) SINGLE USE HYGIENE ARTICLE WITH COMBINED MECHANIC AND ADHESIVE CLOSING SYSTEM

(75) Inventor: Krzysztof Malowaniec, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 09/331,178
(22) PCT Filed: Dec. 4, 1997
(86) PCT No.: PCT/EP97/06773
§ 371 (c)(1), (2), (4) Date: Jun. 23, 1999
(87) PCT Pub. No.: WO98/27922
PCT Pub. Date: Jul. 2, 1998

(30) Foreign Application Priority Data

Dec. 23, 1996 (DE) .......................... 196 54 052

(51) Int. Cl.$^7$ ................................ A61F 13/15
(52) U.S. Cl. ...................... 604/389; 604/391
(58) Field of Search ................ 604/389, 391, 604/386, 387; 428/100, 343; 156/315

(56) References Cited

U.S. PATENT DOCUMENTS 5,961,761 A * 10/1999 Heindel et al. ............. 156/163
6,030,373 A * 2/2000 VanGompel et al. ........ 604/386

FOREIGN PATENT DOCUMENTS

| DE | 29711430 U1 | 10/1997 |
| EP | 0321232 B1 | 6/1989 |
| EP | 0393953 A2 | 10/1990 |
| EP | 0418954 A2 | 3/1991 |
| WO | WO 96/25905 | 8/1996 |

* cited by examiner

Primary Examiner—John G. Weiss
Assistant Examiner—Jacqueline F Stephens
(74) Attorney, Agent, or Firm—Jones,Tullar & Cooper, P.C.

(57) ABSTRACT

The present invention relates to a hygiene article for a single use, in particular disposable nappies or an incontinence product, with a front part, a rear part and an intermediate area for the legs, with closing tabs on the side edges of the rear part for connecting the rear part with the front part in order to seal the article which is placed on a support. The closing tabs have first mechanical closing elements, which cooperate with second mechanical closing elements, fitted to the front part, upon closing of the article. The closing tabs have each at least one adhesive zone, so that they can also be fixed to another part of the article. In order to be able to dispose of the article safely in rolled up state, the article is so designed, according to the invention, that at least one part of the mechanical closing elements of the first type have an adhesive layer at each end opposite the closing tab, and these closing elements at the same time form the adhesive zone, and thus fulfil a mechanical function on closing the article as well as an adhesive function on fixing the closing tabs to another part of the folded or rolled up article, with a view to the disposal of the article.

8 Claims, 2 Drawing Sheets

SINGLE USE HYGIENE ARTICLE WITH COMBINED MECHANIC AND ADHESIVE CLOSING SYSTEM

FIELD OF THE INVENTION

The present invention relates to a single use hygienic item, in particular a disposable diaper or an incontinence product, having a front part, a back part, a step area located between the front part and the back part, and fastening tongues arranged on lateral edges of the rear part for connecting the rear part with the front part for fastening the item placed on a wearer. The fastening tongues have first mechanical fastening elements which work together with second mechanical fastening elements arranged on the front part, and each have at least one adhesively designed area in order to be able to fasten the fastening tongues also to another portion of the item.

BACKGROUND OF THE INVENTION

Known absorbent disposable items, such as diapers, incontinence products or the like, have an absorption body and a front and back part. When placing the item on a wearer, the front and back parts are connected with each by fastening means. The fastening means, which as a rule consist of adhesive strips arranged along the sides, can be released again from the front part for removing the soiled item. For disposal, the used disposable item can then be folded or rolled up into a small package. If the adhesive strips are then applied from the outside on the rolled-up item, there is no danger that the body secretions taken up by the absorbing item are released in the course of throwing the item away.

If the fastening means are designed as adhesive strips, they can be fastened on any arbitrary part of the diaper, i.e. in particular on the item rolled up into a small package. However, adhesive strips have the great disadvantage that they become soiled by oil, lotion, powder or the like and therefore no longer stick together, so that the diaper can no longer be fastened. For this reason, changes are made in that the adhesive strips are being replaced by mechanical fastening means, for example hook- and-eye closures. The adhesive strips are replaced by fastening tongues having first mechanical fastening elements, for example small hooks, which are connected with second mechanical fastening elements, for example eyes arranged on the front part, for fastening the item applied to a wearer. However, in this case the mentioned possibility of keeping the disposable item in the rolled-up state no longer exists, because the fastening tongues having the one elements of the hook-and-eye closure can no longer be fixed on the rolled-up diaper, since the corresponding complementary fastening elements have been rolled up.

To solve this problem, an absorbent disposable item with fastening means is proposed in accordance with European Patent EP 0 321 232, wherein the fastening means have mechanical fastening elements and next to them areas provided with an adhesive, so that the fastening means can also be fixed on the rolled-up item in spite of the mechanical fastening means. In connection with these known fastening means it is disadvantageous that they must be designed correspondingly large, in particular long, so that the mechanical fastening elements as well as the areas covered with adhesive are accommodated. Therefore the corresponding disposable item is not cost-effective.

A fastening system, in particular for hygienic items, having mechanically as well as adhesively cooperating surface structures, which can interact complementarily, is known from European Patent EP 0 418 954 A2.

In connection with a hook-and-eye closure system, Published International Application WO 96/25905 a teaches to provide the hook-forming component as well as the eye-forming component additionally with a cohesion adhesive in order to be able to set the desired adhesive properties (shear forces and stripping forces) between the components of the hook- and-eye closure.

An adhesive coating is known from European Patent EP 0 393 953 a for affixing a sanitary napkin to a piece of clothing, for example. So that the napkin better adheres to the textile material, protrusions are provided on the side of the napkin having the adhesive coating, which are pressed into the textile material and in this way fix the napkin in place secure against sliding. An adhesive layer with protrusions is not suitable for a disposable diaper, which as a rule has plastic foils, but no textile materials, since the protrusions cannot penetrate the foil, so that an adhesive coating of this type cannot be fixed in place on,a disposable diaper.

SUMMARY OF THE INVENTION

Based on this prior art, it is an object of the present invention to make available an improved single use hygienic item, which has improved, simply constructed and dependably fastening tongues with mechanical fastening elements and at least one adhesively embodied area. The item should be dependably disposable, and unintentional opening of the rolled-up or folded-up item should be preventable.

This object is attained by a hygienic item characterized in that at least a portion of the mechanical fastening elements of the first type have a respective adhesive application at their end facing away from the fastening tongue, and these fastening elements simultaneously constitute the adhesively designed area. They therefore have both a mechanical function when fastening the item as well as a simultaneous adhesive function when fastening the fastening tongues on another part of a folded or rolled-up item for disposing of the item.

If at least a part of the fastening elements of the first type have a respective adhesive coating on their end facing away from the fastening tongue, and these fastening elements constitute the adhesively embodied part, these fastening elements have a mechanical function when fastening the item, as well as a simultaneous adhesive function when fixing the fastening tongues on the diaper, which has been rolled up or folded for disposal, at another part outside of the second mechanically acting fastening elements. This results in the further advantage that when placed on the wearer, the diaper can always be securely fastened since, if a fastening tongue is not exactly positioned on the diaper during fastening, for example, so that only a portion of the mechanical fastening elements of the first type can come into engagement with the fastening elements of the second type, the fastening elements of the first type are nevertheless fastened in place on the diaper because of the adhesive coating in accordance with the invention. This advantage cannot be achieved by means of the known areas provided with an adhesive and arranged separately from the mechanical fastening elements of the first type.

Because of the dual function of the first fastening elements, the fastening tongues of the item in accordance with the invention can be made shorter, which results in a savings in material. The adhesively embodied areas will become soiled less rapidly than the known areas provided with adhesive and arranged separately from the mechanical fastening elements, since the soiling by oil, for example, can "run off" from the individual adhesive coating of a fastening elements into the spaces between the fastening elements. But soiling in the spaces does not constitute an interference, so that the item in accordance with the invention is less sensitive to soiling in contrast to soiling of the fastening tongues. Essentially, all fastening elements of the first type have an adhesive coating in order to obtain maximum adhesive force. In a simple embodiment of the invention, the fastening elements of the first type are designed as small hooks. However, preferably the fastening elements of the first type have a mushroom-like shape with a stem and a cap, because in this case it is possible to apply a greater amount of adhesive to the individual fastening elements.

In order to be able to further increase the amount of adhesive applied to the fastening section, the caps of the fastening elements of the first type are flattened, and the fastening section preferably has a T-shape in cross section.

In an embodiment of the invention in accordance with claim 7, a further application of adhesive is provided at least in areas between the fastening elements of the first type, because of which the adhesive force is further increased when the fastening tongue is firmly pressed on the material on which it is to be fastened, so that the fastening elements of the first type are either bent, or penetrate into the material.

The thickness of the further adhesive coating preferably changes in the longitudinal direction of the fastening tongue in order to create areas of different adhesive force.

The thickness of the further adhesive coating preferably decreases in the direction toward the free fastening tongue, so that when the item which has been placed on a wearer is unfastened, the ends of the fastening having less strong adhesive force can be easier undone.

The invention will be explained in detail in what follows by means of exemplary embodiments making reference to the drawings.

DESCRIPTION OF THE PREFERRED EMBODIMENT

Figure 1:
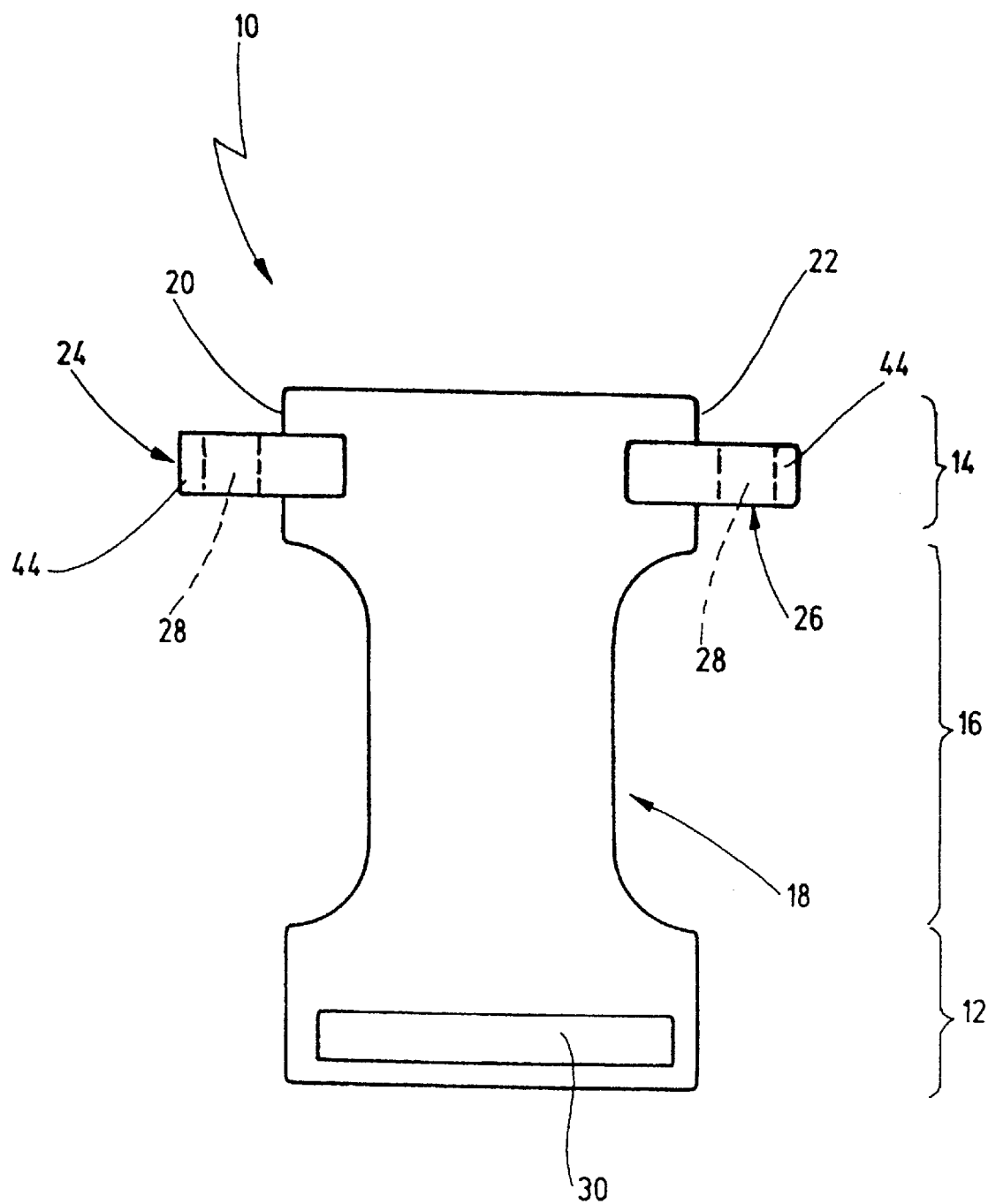
FIG. 1, a hygienic item in accordance with the invention in the flattened-out state.

A single use hygienic item 10 in accordance with the present invention, represented in FIG. 1, can be a disposable diaper, an incontinence product, or the like. The hygienic item will be called a diaper in what follows. Like elements are identified by like reference numerals in the drawing figures.

The diaper 10 is represented in FIG. 1 in the flattened-out state and from the side facing away from the wearer, i.e. the outside. The diaper 10 has a front part 12, a back part 14 and a step area 16 arranged between them. In a known manner, not represented, the diaper 10 is preferably made of a back layer, impervious to liquid, a covering non-woven material pervious to liquids and an absorbent body arranged between them made, for example, of flocked cellulose and, if desired, of super-absorbent materials. Elastic elements can be provided in the area of the cutouts 18 for the legs in the step area 16 for improved sealing of the diaper 10 against the legs of a wearer.

The front part 12 and the back part 14 each have a waist edge and lateral edges 20 and 22. An elastic element can be provided on the front and/or rear waist edge, so that the front and/or the rear waist edge areas are elastically embodied in order to improve the sealing of the diaper 10 against the body of a wearer in the area of the waist.

The diaper 10 furthermore has a fastening tongue 24 and 26 respectively at the lateral edges 20 and 22, by means of which the back part 14 can be connected with the front part 12 via the lateral edges in order to be able to fasten the diaper when attached to the wearer. To this end, the fastening tongues 24 and 26, which are represented in greater detail in FIGS. 2 and 3, can be brought into engagement with at least one fastening section 30, for example a hook-and-eye coating having eyes.

Figure 2:
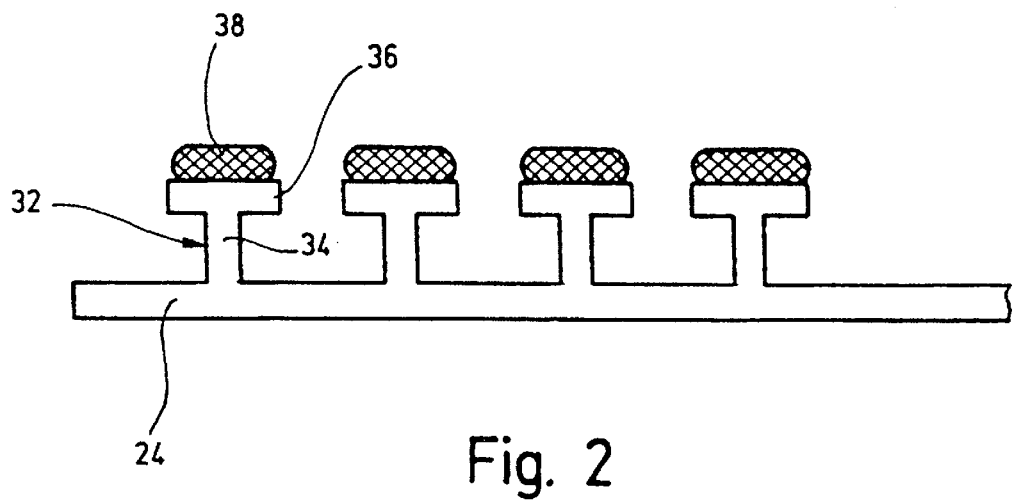
FIGS. 2 and 3, exemplary embodiments of fastening tongues of the hygienic item in cross section.
Figure 3:
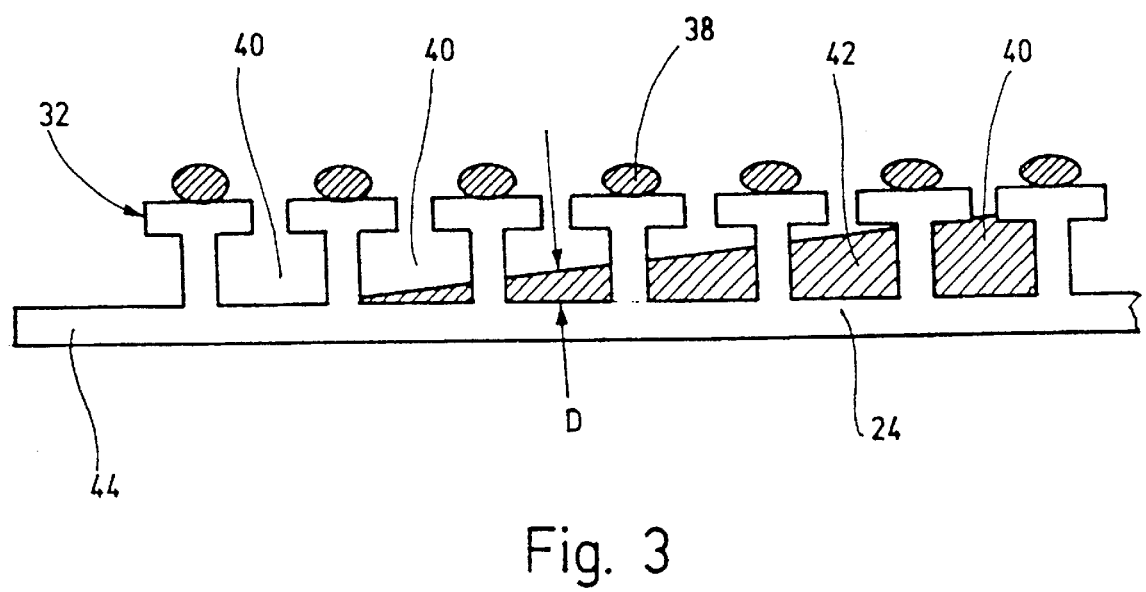

The fastening tongue 24, or respectively 26, is represented enlarged and in cross section in FIGS. 2 and 3. The fastening tongue has mechanical fastening elements 32 of a first type on at least one partial area 28, which can be mechanically connected with fastening elements of a second type, not represented in detail, of the fastening section 30. For example, the fastening elements 32 of the first type can be the small hooks of a known hook-and-eye fastening, which can cooperate with the eyes of the fastening section 30.

However, in a preferred manner the fastening elements 32 of the first type have a mushroom-like shape with a stem 34 and a cap 36, wherein the cap 36 is preferably flattened, and wherein the cross sections of the fastening elements 32 of the first type represented in FIGS. 2 and 3 essentially have a T-shape. These T-shaped fastening elements 32 can cooperate mechanically with the eyes of the fastening section 30, in the same way as the hooks.

In the exemplary embodiment represented, at least a portion of the fastening elements 32 of the first type respectively has an adhesive application 38 on their end facing away from the fastening tongue 24, i.e. on their cap 36. However, preferably essentially all fastening elements 32 have the adhesive application 38. In this case the adhesive application 38 can cover the entire cap 36, or only a portion of the cap 36 (FIG. 3). This is an adhesive bonding agent, so that the fastening tongues 24 and 26 with their fastening elements 32 of the first type can also be fastened outside of the fastening section 30 on another part of the item in order to maintain the item in a folded or rolled-up configuration and to dispose of it dependably. The fastening section 30 having the fastening elements of the second type, is free of adhesive and, together with the fastening elements of the fastening tongues 24 and 26, merely constitutes a mechanical fastening connection.

In a further exemplary embodiment represented in FIG. 3, a further adhesive application 42 is provided at least in areas in the spaces 40 between the fastening elements 32 of the first type. In a preferred manner, the thickness D of this further adhesive application 42 changes in the longitudinal direction of the fastening tongue 24, or respectively 26. In this case it is advantageous if the thickness D is continuously, i.e. gradually, reduced in the direction toward a free tongue end 44. If necessary, the spaces 40 adjoining the free tongue end 44 do not have an adhesive, and the spaces 40 adjoining the tongue end attached to the diaper are essentially completely filled with adhesive.

Preferably the free tongue end 44 has neither mechanical fastening elements nor an adhesive application, and can therefore always be grasped for unfastening the fastened fastening tongue.

What is claimed is:
1. A single use hygiene item, forming at least one of: a disposable diaper and an incontinence product, comprising:

a front part having mechanical fastening elements free of adhesive;

a back part defining lateral edges; and fastening tongues extending from each lateral edge of said back part for connecting said back part to said front part for fastening the item placed on a wearer, said fastening tongues each have a base surface and first mechanical fastening elements extending therefrom which operate with said mechanical fastening elements of said front part, which serve as second mechanical fastening elements when fastening the item, said first mechanical fastening elements extending to an effective height from said base surface of said fastening tongues to a free end facing away from said base surface and at least one adhesively designed area to enable fastening of said fastening tongues also to another portion of the item outside said second mechanical fastening elements, wherein at least a portion or all of said first mechanical fastening elements have a respective adhesive application at their end facing away from said base surface, wherein said first mechanical fastening elements simultaneously constitute said adhesively designed area so that they therefore have both a mechanical function for operating with said second mechanical fastening elements of said front part when fastening the item and an adhesive function for item disposal by adhesively adhering the fastening tongues to another portion outside those second mechanical fastening elements of said front part.

2. The hygienic item as defined in claim 1, wherein said first mechanical fastening elements comprise small hooks.

3. The hygienic item as defined in claim 1, wherein said first mechanical fastening elements have a mushroom-like shape with a stem and a cap.

4. The hygienic item as defined in claim 1, wherein said cap has a flattened configuration.

5. The hygienic item as defined in claim 1, wherein said first mechanical fastening elements have a T-shaped cross section.

6. The hygienic item as defined in claim 1, further comprising:

an adhesive provided at least in areas between said first mechanical fastening elements.

7. A single use hygiene item, forming at least one of: a disposable diaper and an incontinence product, comprising:

a front part having mechanical fastening elements;

a back part defining laterally edges;

fastening tongues extending from each lateral edge of said back part for connecting said back part to said front part for fastening the item placed on a wearer, said fastening tongues each have a base surface first mechanical fastening elements extending therefrom which operate with said mechanical fastening elements of said front part, which serve as second mechanical fastening elements when fastening the item, and at least one adhesively designed area to enable fastening of said fastening tongues also to another portion of the item; and an adhesive provided at least in areas between said fastening elements of the first type, wherein at least a portion of said first mechanical fastening elements, or said mechanical fastening elements of a first type, have a respective adhesive application at their end facing away from said fastening tongue, wherein said first mechanical fastening elements simultaneously constitute said adhesively designed area so that they therefore have both a mechanical function and an adhesive function for item disposal, and wherein the thickness of said adhesive changes in the longitudinal direction of said fastening tongue.

8. The hygienic item as defined in claim 7, wherein the thickness of said adhesive continuously decreases in the direction toward the free end of said fastening tongue.

* * * * *